United States Patent [19]

Patchett et al.

[11] Patent Number: 4,602,002
[45] Date of Patent: Jul. 22, 1986

[54] N-CARBOXYMETHYL SUBSTITUTED LYSYL AND α-(ε-AMINOALKYL) GLYCYL AMINO ACID ANTIHYPERTENSIVE AGENTS

[75] Inventors: Arthur A. Patchett, Westfield; Mu T. Wu, Clark, both of N.J.

[73] Assignee: Merck & Co., Inc., Rahway, N.J.

[21] Appl. No.: 463,412

[22] Filed: Feb. 7, 1983

[51] Int. Cl.[4] .................. A61K 31/405; A61K 37/02; C07D 207/08
[52] U.S. Cl. ........................................ 514/11; 514/10; 544/50; 260/998.2; 546/147; 546/165; 546/245; 546/341; 548/186; 548/188; 548/201; 548/379; 548/408; 548/452; 548/491; 548/899; 548/532
[58] Field of Search ................ 260/112.5 R; 424/258; 514/11

[56] References Cited
U.S. PATENT DOCUMENTS 4,470,973 9/1984 Natarajan et al. ............... 260/112.5

Primary Examiner—Glennon H. Hollrah
Assistant Examiner—James H. Turnipseed
Attorney, Agent, or Firm—Salvatore C. Mitri; Michael C. Sudol

[57] ABSTRACT

Compounds of the formula:

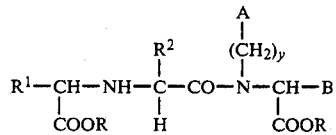

wherein
R[2] is —(CH$_2$)$_k$—X—(CH$_2$)$_j$—NHR[3]; wherein k is 0 to 3, j is 1 or 2; X is F or OH; and, R[3] is hydrogen; loweralkyl or loweraralkyl which may be substituted by hydroxy, carboxy, carbamoyl, or carbalkoxy; or, acyl; and, a pharmaceutically acceptable salt thereof; are inhibitors of angiotensin I converting enzyme useful as antihypertensive agents.

5 Claims, No Drawings

N-CARBOXYMETHYL SUBSTITUTED LYSYL AND α-(ε-AMINOALKYL) GLYCYL AMINO ACID ANTIHYPERTENSIVE AGENTS

BACKGROUND OF THE INVENTION

1. Field of the Invention

The present invention is concerned with novel N-carboxymethyl substituted lysyl and α-(ε-aminoalkyl)glycyl amino acid compounds which are effective inhibitors of angiotensin I converting enzyme. These novel compounds are, consequently, combined with pharmaceutically acceptable carriers to form pharmaceutical compositions of the present invention and are used in a method of treating hypertension.

Angiotensin II, a powerful vasoconstrictor hormonal peptide, is formed from the inactive angiotensin I by the action of angiotensin-converting enzyme. Recently, potent inhibitors of angiotensin-converting enzyme have been reported which are capable of lowering the blood pressure in hypertensive patients. The novel N-carboxymethyl substituted lysyl and α-(ε-aminoalkyl)glycyl amino acid compounds of the present invention are also potent inhibitors of angiotensin-converting enzyme.

2. Brief Description of the Prior Art

U.S. Pat. Nos. 4,113,715; 4,129,571; and 4,154,960 disclose substituted acyl derivatives of amino acids which are useful as angiotension converting enzyme inhibitors. More specifically, these compounds are mercapto substituted acyl amino acids and derivatives thereof including the clinically effective antihypertensive compound, captopril, i.e., D-3-mercapto-2-methylpropanoyl-L-proline.

The foregoing prior art compounds are not dipeptide derivatives as are the compounds of tne present invention. Furthermore, these prior art compounds contain an essential sulfhydryl substituent or derivative thereof whereas those of the present invention do not. In addition, the dipeptide compounds of the present invention are unusual dipeptides whose N-terminus bears a carboxymethyl group which is preferably further substituted on the methyl group. In addition, the carboxyl group(s) may also be converted to ester, amide and salt derivatives. In effect, the compounds of the present invention are hybrids formed by fusing α-amino acids onto dipeptides by means of a nitrogen shared by these two part-structures. This structural arrangement is rare in the field of synthetic and natural peptides and is not suggested or disclosed by the mercaptoacyl type functions of the two prior art patents identified above.

U.S. Pat. No. 4,052,511 discloses N-carboxyalkanoylamino acids which are useful as angiotensin converting enzyme inhibitors. Since the compounds of the present invention are dipeptide derivatives, in a formal sense they may be considered to be related to some of the compounds disclosed in U.S. Pat. No. 4,052,511. However, when a particular one of the methylene groups is replaced by an amino function as in the present invention, compounds of surprisingly high potency are obtained. For example, the preferred compounds of the present invention can be administered in dosages as low as about 2.5 mg per patient per day as opposed to the lowest dosage level of 1 mg per kg per day for preferred compounds disclosed in the U.S. Pat. No. 4,052,511 which is about equivalent to 60 mg per patient per day based on an average patient weight of about 150 pounds.

DETAILED DESCRIPTION OF THE INVENTION AND PREFERRED EMBODIMENTS

In its broadest aspect, the present invention relates to novel N-carboxymethyl substituted lysyl and α-(ε-aminoalkyl)glycyl amino acid compounds of the formula:

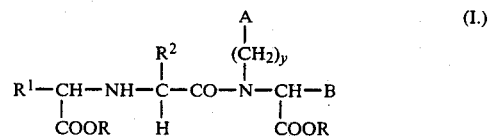

wherein:
R is hydrogen; loweralkyl; aralkyl; or, aryl;
$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino; acylamino substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di-, or trisubstituted by loweralkyl, hydroxy, loweralkoxy, halo, amino, acylamino, lower alkylthio or aminoloweralkyl; benzofused cycloalkyl or bicycloalkyl of from 8 to 12 carbon atoms; arloweralkyl, arloweralkenyl, heteroloweralkyl and heteroloweralkenyl in which the aryl or heteroaryl rings may be mono-, di-, or trisubstituted by halo, lower alkyl, hydroxy, loweralkoxy, amino, lower alkylamino, diloweralkylamino, aminolower alkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n-Q-(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, or $SO_2$, $N-R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl; in the group $$\begin{array}{c} A \\ | \\ (CH_2)_y \\ | \\ -N-CH\ B \\ | \\ COOR \end{array} \quad (5)$$

y is 0 to 4
A is
- (a) alkyl, including branched unsaturated and cyclic alkyl of 3 to 8 carbon atoms;
- (b) benzofused cycloalkyl or bicycloalkyl of 8 to 12 carbon atoms;
- (c) aryl or heteroaryl groups which may be mono-, di-, or trisubstituted by loweralkyl, loweralkoxy, halo, amino, acylamino, hydroxy, acyl or acyloxy, and corresponding groups in which the aryl or heteroaryl groups are partially or completely hydrogenated;
- (d) lower alkyl including branched and unsaturated groups which may be substituted by aryl or heteroaryl groups and corresponding groups in which the aryl or heteroaryl rings are partially or completely hydrogenated;

B is hydrogen or loweralkyl
or
A and B may be joined, together with the carbon atoms to which they are attached to form a ring having the formulae:

$$\begin{array}{c} R_5 \\ | \\ (CH)_q-X-Y \\ N\diagup \qquad \qquad | \\ \diagdown \qquad \quad (CH)_p \\ \qquad \qquad \qquad | \\ \qquad \qquad \qquad R_5 \end{array} \quad (1)$$

wherein X and Y taken together are $$-CH_2CH_2-,\ \begin{array}{c}CH-S-\\|\\R_6\end{array},\ \begin{array}{c}R_7\ O\\|\ \ ||\\-C-C-\\||\ \ |\\O\ R_6\end{array},\ \begin{array}{c}-CH-C-\\|\\R_6\end{array}$$

$$\begin{array}{c}O\\||\\-C-O-,\end{array}\ \begin{array}{c}O\\||\\C-S-,\end{array}\ \begin{array}{c}R^7\\|\\-CH_2C-\\|\\R^6\end{array},\ \begin{array}{c}R^7\\|\\-C-CH_2-\\|\\R^6\end{array}$$

$$\begin{array}{c}O\ R^7R^6\\||\ \ |\ \ |\\-C-N,\ CH-CH,\end{array}\ -N=CH-\ \text{or}\ -CH=N-$$

wherein:
$R^5$ and $R^6$ individually are hydrogen; lower alkyl; cycloalkyl; aryl; aralkyl; heteroaryl; lower alkyloxy, lower alkylthio; aryloxy; arylthio; arloweralkyloxy; arlower alkylthio; hydroxy; acyloxy; acyllower alkyl; halo; amino; mono- or disubstituted lower alkyl amino; arlower alkylamino; heteroloweralkylamino; acylamino in which the acyl group may be lower alkanoyl, aroyl, heteroaroyl or heterolower alkanoyl; carbamoyl; or N-substituted carbamoyloxy; and wherein any of these groups containing an aromatic ring, said ring may be mono-, di-, or trisubstituted by lower alkyl, lower alkoxy, loweralkylthio, halo, hydroxy, aryl, aryloxy, arylthio or aralkyl; and wherein any of said groups containing an aryl or heteroaryl group in which said groups are partially or completely hydrogenated;

$R^7$ is hydrogen, loweralkyl, aryl, cycloalkyl, or substituted aryl wherein the substituent can be halo, hydroxy, alkoxy, amino or loweralkyl;
or
$R^6$ and $R^7$ taken together may be oxo, or, together with the atoms to which they are attached form a 3 to 6 membered ring which may contain 0, 1, or 2 atoms of N, S, or O;

p and q are independently 0 to 3;

$$\begin{array}{c}CH_2---C-R^6\\ \diagup \qquad \quad ||\\ N\\ \diagdown\\ -(CH_2)_s-C-R^7\\ | \\ H \end{array} \quad (2)$$

wherein $R^6$ and $R^7$ are as defined above and s is 0, 1, and 2;

$$-N\diagup\stackrel{W}{\diagdown}\stackrel{R^8}{\diagdown}\diagup \quad \text{or} \quad -N\diagup\stackrel{W}{\diagdown}\stackrel{R^8}{\diagdown}()_s$$
$$\quad |\qquad\qquad\qquad\qquad\qquad |$$
$$\quad H\ \ Z\qquad\qquad\qquad\qquad H\ \ Z$$

wherein
W is absent;

$$\begin{array}{c}O\\||\\-C-\end{array},$$

N or S;
Z is $-(CH_2)_t-$, where t is 0 to 2, provided that t may not be 0 when W is absent; $-O-$; $-N-$, or $-S-$;
$R^8$ is hydrogen; lower alkyl; loweralkoxy; hydroxy; halo, lower alkylthio; amino; acylamino; or cyano; s is 1 to 3;
$R^2$ is $(-CH_2)_k-X-(CH_2)_j-NHR^3$; wherein k is 0 to 3; j is 1 or 2; and, $R^3$ is hydrogen; loweralkyl or loweraralkyl which may be substituted by hydroxy, carboxy, carbamoyl, or carbalkoxy; or, acyl; X is FCH or HOCH; and, a pharmaceutically acceptable salt thereof.

The alkyl substituents recited above denote straight and branched chain hydrocarbons of $C_1$ to $C_{12}$ such as methyl, hexyl, propyl, docecyl isopentyl, isopropyl, neopentyl etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon carbon double bond or triple bond, respectively, such as vinyl, 2-butenyl and 1-hexynyl.

Cycoalkyl denotes rings composed of 5 to 8 methylene groups, each of which may be substituted or unsubstituted with other hydrocarbon substituents, such as, for example, cyclopentyl, cycloheptyl, 4-methyl cyclohexyl and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, such as, for example, indolyl, quinolinyl, isoquinolinyl, benzimidazolyl, benzothiazolyl, benzthienyl, and naphthyridyl.

The acylamino substituent represents loweralkanoylamino and aroylamino.

Of the various heterocyclic elements generally defined above as

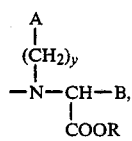

the following are specifically included and are preferred:

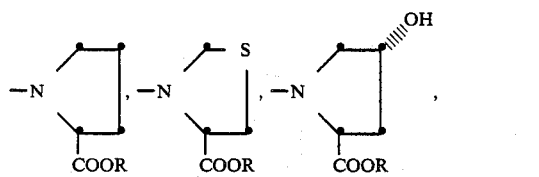

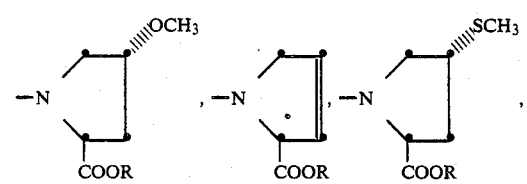

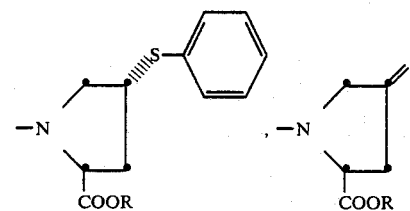

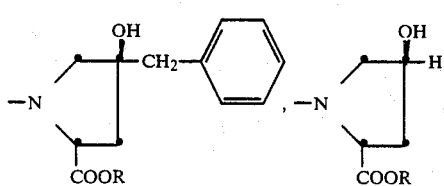

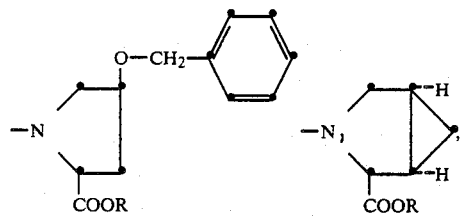

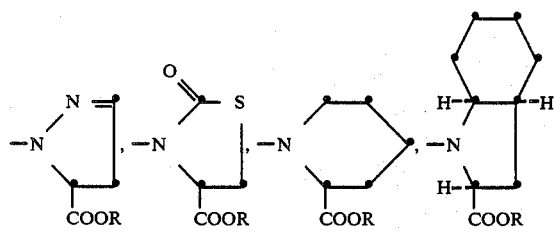

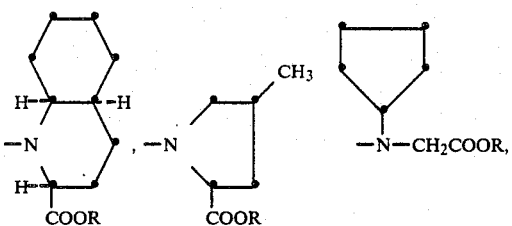

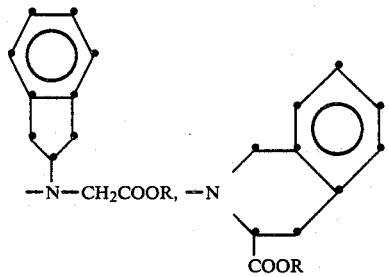

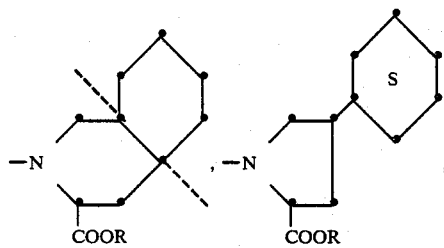

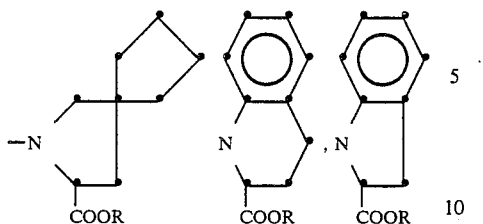

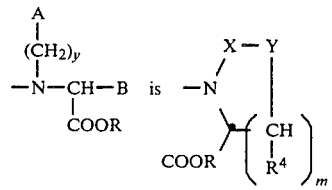

where X and Y taken together are —CH$_2$—CH$_2$—; R$^4$ is hydrogen; m is 1; and R is as defined above;

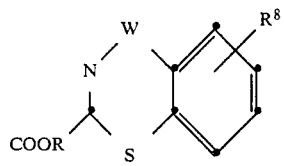

wherein W and Z are CH$_2$; and, R$^8$ is H;

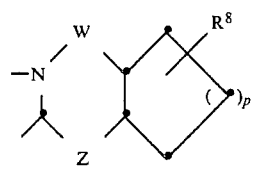

wherein W is O; Z is CH$_2$; p is 2; and, R$^8$ is H;

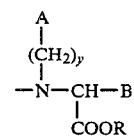

wherein y is O; A is 2-indanyl;
B is H; and, R is as defined above.

Especially preferred compounds of the present invention are the following:

N$^2$-[1(S)-carboxy-3-phenylpropyl]-(4-hydroxy-L-lysyl)-L-proline;

N-[1(S)-ethoxycarbonyl-3-phenylpropyl]-[5-hydroxy-L-lysyl]-L-proline;

N-[1(S)-carboxy-3-phenylpropyl]-(4-fluoro-L-lysyl)-L-proline;

N-[1(S)-carboxy-3-phenylpropyl]-(3-fluoro-L-ornithyl)-L-proline;

N-[1(S)-carboxy-3-phenylpropyl]-(4-hydroxy-L-lysyl)-(N-2-indanyl)glycine;

N-[1(S)-carboxy-3-phenylpropyl]-(4-fluoro-L-lysyl)-(N-2-indanyl)glycine;

N-[1(S)-carboxy-3-phenylpropyl]-(3-fluoro-L-ornithyl)-(N-2-indanyl)glycine;

N-[1(S)-carboxy-3-phenylpropyl]-(4-hydroxy-L-lysyl)-perhydroindole-2-carboxylic acid;

N-[1(S)-carboxy-3-phenylpropyl]-(4-fluoro-L-lysyl)-perhydroindole-2-carboxylic acid;

N-[1(S)-carboxy-3-phenylpropyl]-(3-fluoro-L-ornithyl)-perhydroindole-2-carboxylic acid;

N$^2$-[1(S)-carboxy-3-phenylpropyl]-(4-hydroxy-L-lysyl)-1,2,3,4-tetrahydroisoquinoline-3-carboxylic acid;

N$^2$-[1(S)-carboxy-3-phenylpropyl]-(4-fluoro-L-lysyl)-1,2,3,4-tetrahydroisoquinoline-3-carboxylic acid;

The Formula I compunds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfoate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

Preferred compounds of the present invention are those of Formula I wherein:

R is hydrogen or loweralkyl;

R$^1$ is alkyl of 1-10 carbon atoms which include branched, cyclic and unsaturated alkyl groups; substituted loweralkyl wherein the substituent can be hydroxy, lower alkylthio, amino, alkylamino, lowerdialkylamino, and acylamino; substituted loweralkyl having the formula R$_A^1$(CH$_2$)$_n$—Q—(CH$_2$)$_m$—wherein n is 0-2, m is 1-3, R$_A^1$ is aryl or heteroaryl optionally substituted by alkyl, halo, dihalo, amino, cyano, hydroxy, or alkoxy, and Q is O, S, N—R$_B^1$, CONR$_C^1$, NR$_C^1$CO, or CH=CH wherein R$_B^1$ is hydrogen, loweralkyl, aralkyl, loweralkanoyl, or aroyl and R$_C^1$ is hydrogen or loweralkyl; aralkyl or heteroaralkyl which include branched loweralkyl groups; substituted aralkyl or substituted heteroaralkyl which include branched loweralkyl groups wherein the loweralkyl substituents can be amino, acylamino, or hydroxy and the aryl and heteroaryl substituents can be loweralkyl, halo, dihalo, amino, cyano, hydroxy, loweralkoxy, aminoloweralkyl, or hydroxyloweralkyl.

R$^2$ is —(CH$_2$)$_k$—X—(CH$_2$)$_j$—NH$_2$; wherein k is 2, j is 1, and X is as defined above; and, and N²-[1(S)-carboxy-3-phenylpropyl]-(3-fluoro-L-ornithyl)-1,2,3,4-tetrahydroisoquinoline-3-carboxylic acid.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodilator peptide, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzme inhibition assays. For example, a useful method is that of Y. Piquilloud, A. Reinharz and M. Roth, *Biochem. Biophys. Acta,* 206, 136 (1970) in which the hydrolysis of carbobenzyloxyphenylalanyl-histidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

Thus, in accordance with the present invention there is provided a pharmaceutical composition comprising a pharmaceutically acceptable carrier and a therapeutically effective amount of a compound of Formula I.

There is also provided, in accordance with the present invention, a method of treating hypertension comprising administering to a patient in need of such treatment a therapeutically effective amount of a compound of Formula I.

For the purpose of treating hypertension, and those clinical conditions noted above, the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hyroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures by liquid at the rectal temperature and will therefore melt in the rectum to release the drug. Such materials are cocoa butter and polyethylene glycols.

Dosage levels of the order of 1 to 200 mg per patient per day, in single or multiple doses, are useful in the treatment of the above indicated conditions. Preferably, the dosage range will be from 2.5 to 100 mg per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention can also be administered in combination with other antihypertensives and/or diuretics. For example, the compounds of this invention can be given in combination with such compounds as acetazolamide, amiloride, aminophylline, atenolol, bendroflumethiazide, benzthiazide, bumetanide, chlorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)ethyl]amino]-3-[[4-(2-thienyl)-1H-imidazol-2-yl]phenoxy]-2-propanol, ethacrynic acid, flumethiazide, furosemide, guanethidene sulfate, hydralazine hydrochloride, hydrochlorothiazaide, hydroflumethiazide, (+)-4-[3-[-[2-(1-hydroxycyclohexyl)ethyl]-4-oxo-2-thiazolidinyl]propyl]-benzoic acid, indacrinone and variable ratios of its enantiomers, merethoxylline procaine, methylclothiazide, methyldopa, methyldopate hydrochloride, metolazone, metoprolol tartate, minoxidil, naldolol, nifedipine, pargyline hydrochloride, pindolol, polythiazide, prazosin, propranolol, quinethazone, *Rauwolfia Serpentina*, rescinnamine, reserpine, sodium ethacrynate, sodium nitroprusside, spironolactone, ticrynafen, timolol, triamterene, trichlormethiazide, trimethophan camsylate, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective in the 2.5 to 100 mg per day range can be effectively combined at levels at the 0.5 to 100 mg per day range with the following compounds at the indicated per day dose range: hydrochlorothiazide (10–100 mg); chlorothiazide (125–2000 mg); manipulated indacrinone enantiomer ratio (25–150 mg); ethacrynic acid (15–2000 mg); amiloride (5–20 mg); furosemide (5–80 mg); propranolol (20–480 mg); timolol (5–60 mg); and methyldopa (65–2000 mg); and the pivaloyloxyethyl ester of methyldopa (30–1000 mg). In addition, triple drug combinations of hydrochlorothiazide (10–100 mg) plus amiloride (5–20 mg) plus converting enzyme inhibitor of this invention (0.5–100 mg); hydrochlorothiazide (10–100 mg) plus timolol (5–60 mg) plus the converting enzyme inhibitor of this invention (0.5–100 mg); or manipulated indacrinone enantiomer ratio (25–150 mg) plus amiloride (5–20 mg) plus converting enzyme inhibitor of this invention (0.5–100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of a compound or mixture of compounds of Formula I or a physiologically acceptable salt is compounded with a physiologically acceptable vehicle, carrier, excipient, binder, preservative, stablizer, flavor, etc., in a unit dosage form as called for by accepted pharmaceutical practice. The amount of active substance in these compositions or preparations is such that a suitable dosage in the range indicated is obtained.

The compounds of Formula I can be prepared by one or more of the methods described further below.

As will be evident to those skilled in the art and as demonstrated in the Examples which follow, reactive groups not involved in the reactions, such as amino, carboxy, mercapto, etc., may be protected by methods standard in peptide chemistry prior to the coupling reactions and subsequently deprotected to obtain the desired products.

are first protected with BOC and CBZ while proline is coupled to the carboxyl group. The $N^2$ BOC protecting group is then removed and the 1-carboxy-3-phenylpropyl group is coupled. Finally, the CBZ protecting group is removed from the $N^6$ amino group.

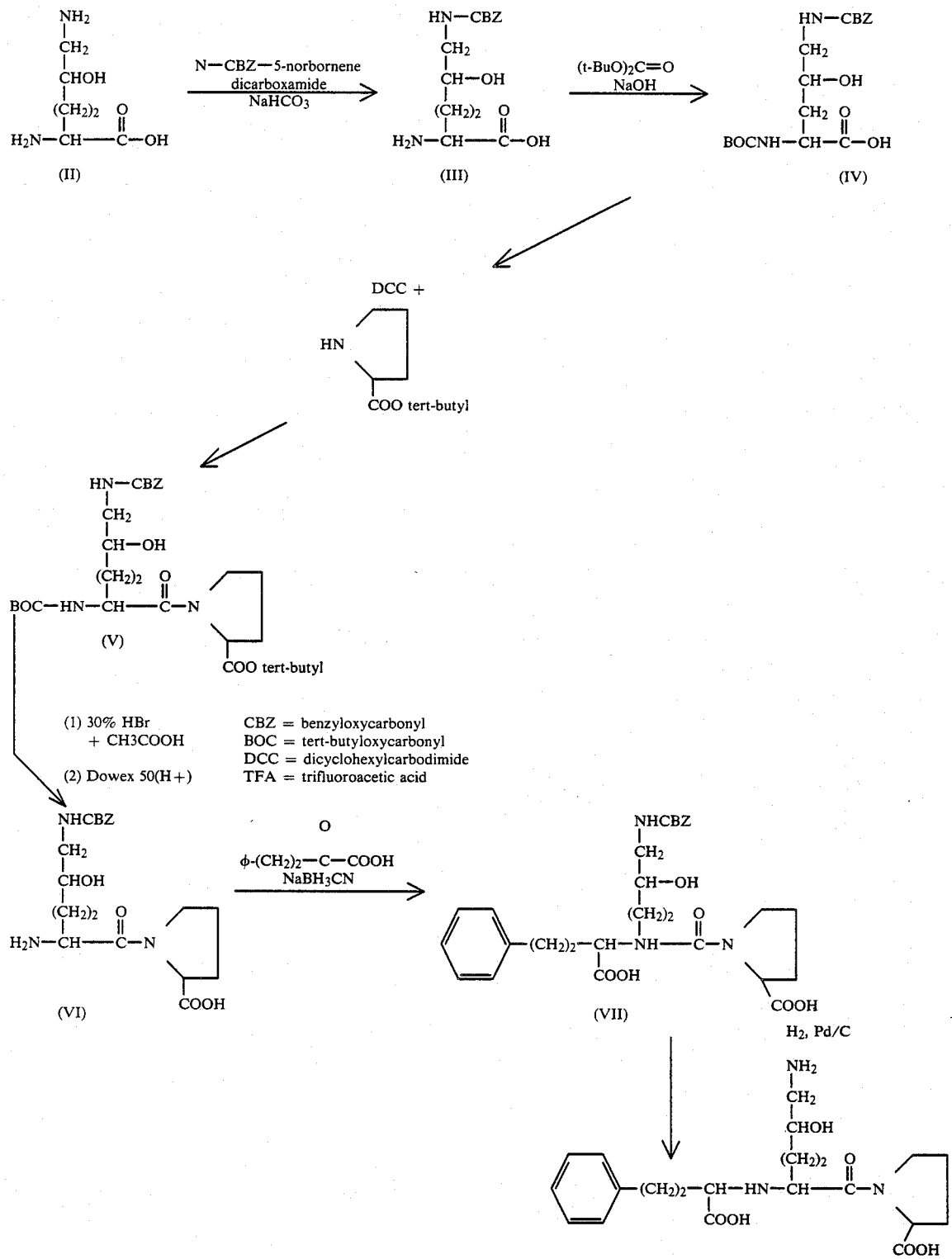

In the reactions illustrated above, the starting material of Formula II, 5-hydroxy-L-lysine, is a commercially available material. The $N^2$ and $N^6$ amino groups The same sequence of reactions and the same reaction conditions can be used to prepare compounds of Formula I which contain fluoro lysine in place of the hydroxy lysine moieties. Starting materials such as 4-fluoro-lysine and 3-fluoro-ornithine can be employed and these starting materials can be prepared according to the procedures and methods described in copending application Ser. No. 403,890, filed July 30, 1982.

The following examples are set forth to further illustrate the methods described herein for preparing the novel peptides of the present invention.

EXAMPLE 1

N-[6-Amino-2-(1-carboxy-3-phenylpropylamino)-5-hydroxyhexanoyl]-L-proline

Step A: N-Benzyloxycarbonyl-5-hydroxylysine (III)

Sodium bicarbonate (4.2 g, 0.050 mol) and 5-hydroxylysine hydrochloride (2.50 g, 0.0126 mol) were dissolved in water (70 ml) with stirring at room temperature. Acetonitrile (40 ml) was added, followed by N-benzyloxycarbonyloxy-5-norbornen-2,3-dicarboximide (3.94 g, 0.0126 mol) in acetonitrile (30 ml) over 15 minutes. After 2 hours, most of the acetonitrile was removed in vacuo and the remaining solution was treated with hydrochloric acid to reduce the pH to 2.0. The solution was extracted with ethyl acetate (50 ml), the pH was increased to 5.5 with sodium hydroxide, and the product was purified over Dowex 50W-2X. The product was eluted with 3% pyridine in water, concentrated to a small volume and freeze dried to give III (1.24 g, 0.0042 mol, 33%); nmr (0.5 M NaOD in $D_2O$)$\delta$ 1.4–2.1 (m, 4H, —$CH_2CH_2$—), 3.1–3.5 (m, 2H, —$NCH_2CH$ ), 3.5–3.9 (m, $\overline{1H}$, —$\overline{NCHRCO}$), 3.9–4.2 (m, 1$\overline{H}$, —$CH_2$-$\underline{CHOHCH_2}$—), 5.10 (s, 2H, —$CH_2\phi$), 7.39 (s, 5H, —$CH_2\phi$); mass spectrum (FAB): $\overline{297}$ (M+1).

Step B:
6-Benzyloxycarbonylamino-2-tert-butyloxy-carbonylamino-5-hydroxy-hexanoic acid (IV)

A solution of III (1.24 g, 0.0042 mol) in aqueous sodium hydroxide (1.5 ml of 2.77 N and 15 ml of water) was cooled to 15° and was diluted with tert-butyl alcohol (12 ml). Di-tert-butyl-dicarbonate (1.00 g, 0.0046 mol) was added in one portion, and the mixture was stirred for 1 hour. The mixture was concentrated in vacuo to a small volume to remove the alcohol and the residue was diluted with water (25 ml), acidified to pH 2.0 and extracted wth ethyl acetate (50 ml). After concentration in vacuo a colorless oil remained. (IV, 1.45 g, 0.0037 mol, 87%). NMR and mass spectrum were consistent with the structure.

Step C:
N-(6-Benzyloxycarbonylamino-2-tert-butyloxy-carbonylamino-5-hydroxy-hexanoyl)-L-proline-tert-butyl ester (V)

Compound IV (0.50 g, 0.00216 mol) and L-proline tert-butyl ester (0.22 g, 0.0013 mol) were dissolved in methylene chloride (15 ml) and the solution was cooled to 0° and was treated with dicyclohexylcarbodiimide (0.27 g, 0.0013 mol). After allowing to warm with stirring overnight, the mixture was filtered. The filtrate was concentrated and purified over LH-20 to give V.

Step D:
N-(2-Amino-6-benzyloxycarbonylamino-5-hydroxyhexanoyl)-L-proline (VI)

Compound V was dissolved in trifluoroacetic (10 ml) and the solution was stirred 30 minutes at room temperature. The solvent was removed in vacuo to give crude VI.

Step E:
N-[6-Benzyloxycarbonylamino-2-(1-carboxy-3-phenyl-propylamino)-5-hydroxyhexanoyl]-L-proline (VII)

Compound VI and 4-phenyl-2-oxobutanoic acid (5 eq) were mixed with water (10 ml) and concentrated NaOH was added to raise the pH to 7.5. Ethanol was added (10 ml) and a solution of sodium cyanoborohydride (3 eq) in ethanol (4 ml) was added dropwise over 15 hours. Dowex 50W-2X (H+) (25 cc) was added with stirring. After 1 hour, the slurry was added to a column of Dowex (50 cc), the column was washed with ethanol and water and the product was eluted with 3% pyridine in water. After concentration and purfication over an LH-20 column, freeze drying gave V.

Step F:
N-[6-Amino-2-(1-carboxy-3-phenylpropylamino)-5-hydroxyhexanoyl]-L-proline (VIII)

Compound VII in ethanol was hydrogenated at 40 psi at room temperature for 24 hours using 10% Pd/C. Filtration, purification over LH-20 and freeze drying gave VIII.

EXAMPLE 2

$N^2$-[1(S)-Carbethoxy-3-phenylpropyl]-[5-hydroxy-DL-lysyl]-L-proline

In the manner as described in Example 1, Step E, $N^6$-benzyloxycarbonyl-5-hydroxy-DL-lysyl-L-proline and 2-oxo-4-phenylbutyric acid ethyl ester are condensed in the presence of sodium cyanoborohydride. The reaction is followed by the removal of the benzyloxycarbonyl group with 30–32% HBr in glacial acetic acid to afford the title compound.

EXAMPLE 3

Additional products of Formula I can be prepared by employing the keto acids and keto esters listed in Table I below. These are condensed with the desired intermediate, for example $N^6$-benzyloxycarbonyl-5-hydroxy-DL-lysyl-L-proline, in the presence of sodium cyanoborohydride, in accordance with the procedures described in the Examples above. The $N^6$-benzyloxycarbonyl group is then removed to give the desired product.

The desired intermediate will be of the formula:

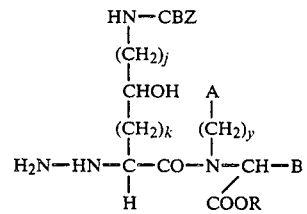

and the keto acids and keto esters will be of the formula:

R'COCOOR, where the various substituents have the same meaning as in Formula I.

TABLE I

Keto Acids and Esters of the Formula R'COCOOR

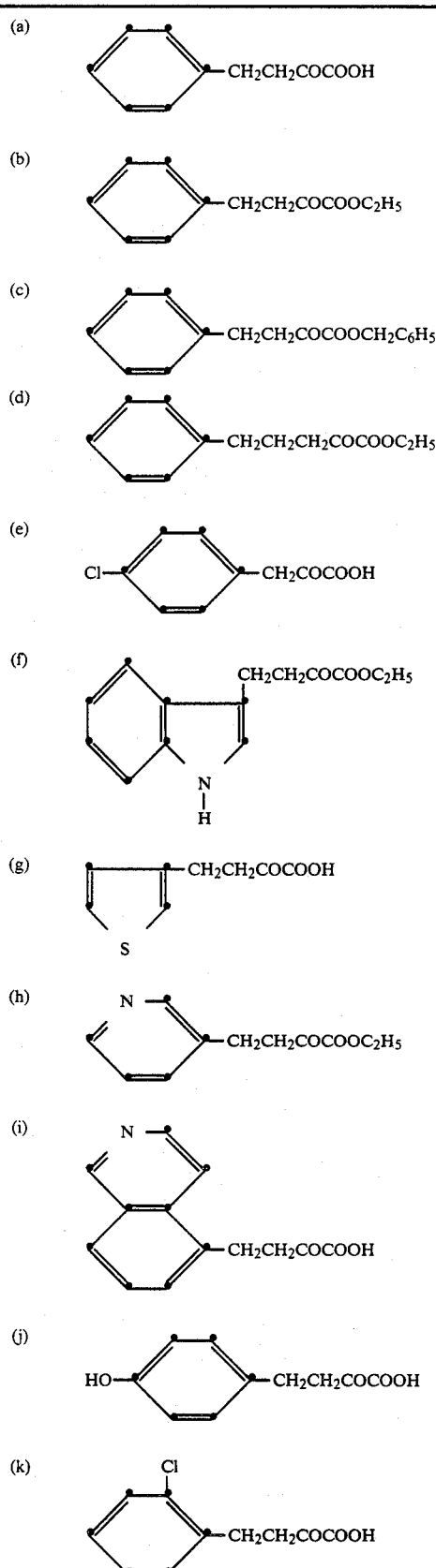

TABLE I-continued

Keto Acids and Esters of the Formula R'COCOOR

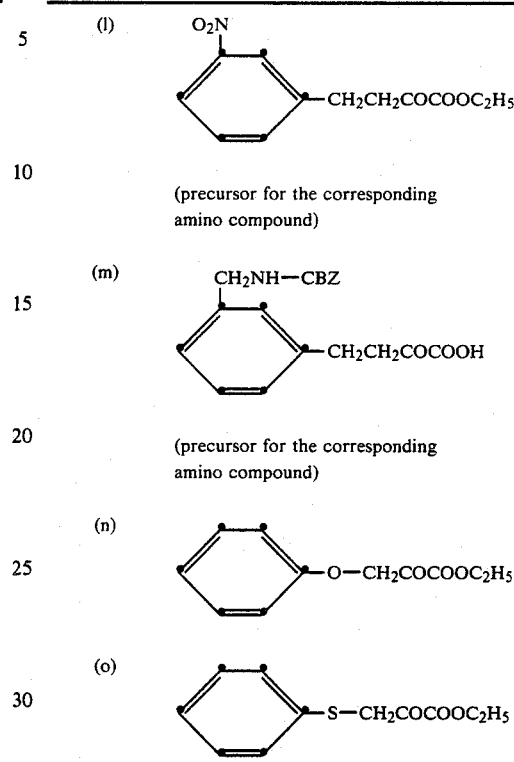

(l) precursor for the corresponding amino compound (m) precursor for the corresponding amino compound Additional examples of the compounds of Formula I which can be synthesized by the procedures described above are illustrated by, but not limited to, the compounds illustrated in Table II below:

TABLE II

Additional Examples of Compounds of Formula I:

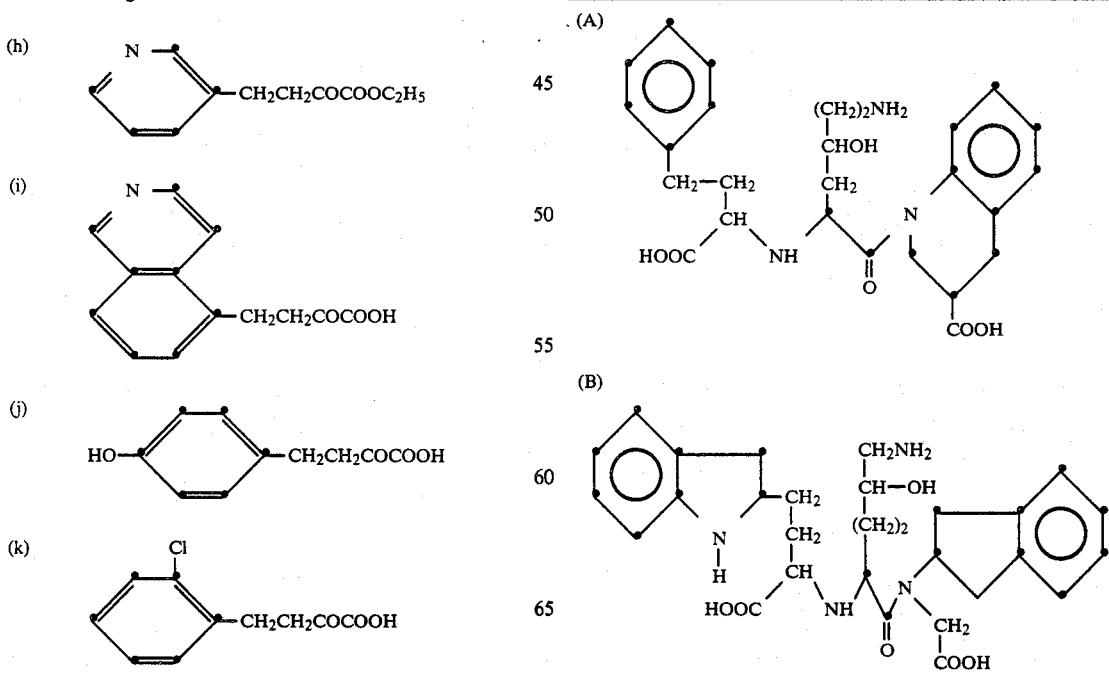

TABLE II-continued
Additional Examples of Compounds of Formula I:
(C) 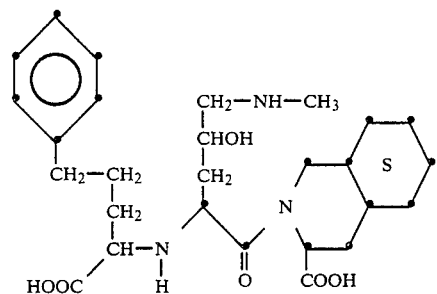
(D) 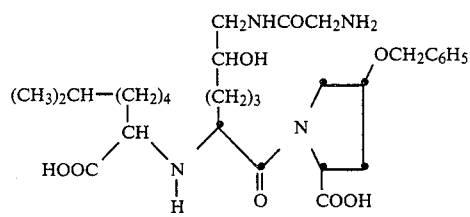
(E) 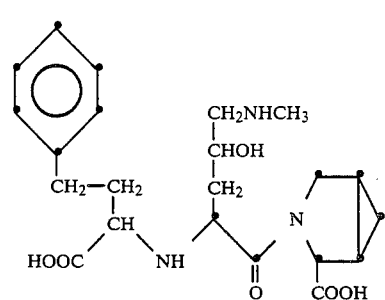
(F) 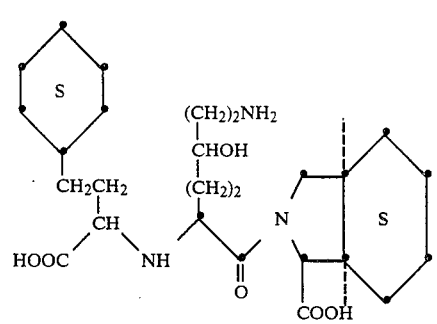
(G) 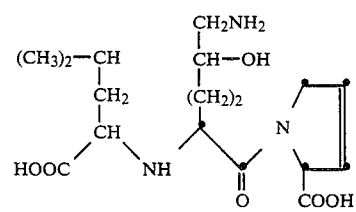
(H) 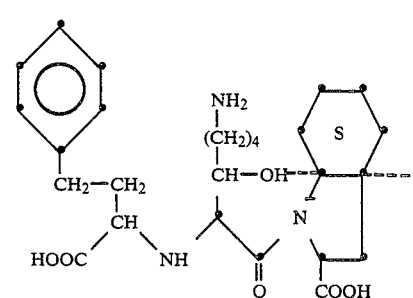
(I) 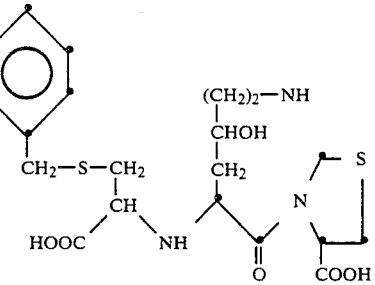
(J) 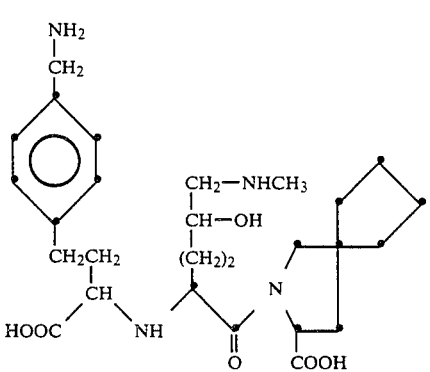
(K) 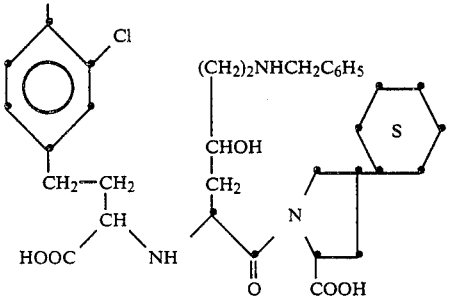
(L) 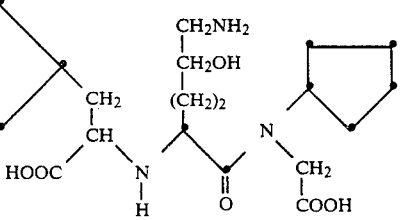
(M) 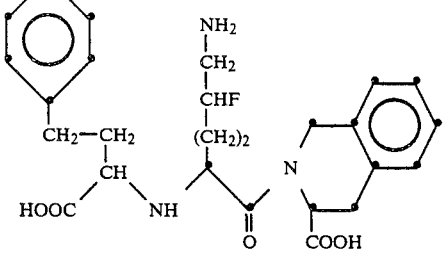
(N)

TABLE II-continued
Additional Examples of Compounds of Formula I:

(O)
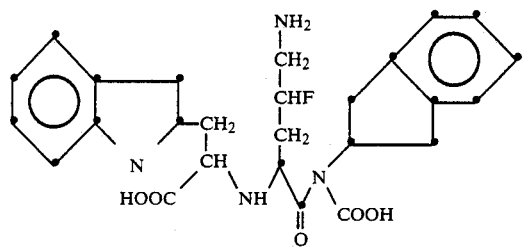

(P)
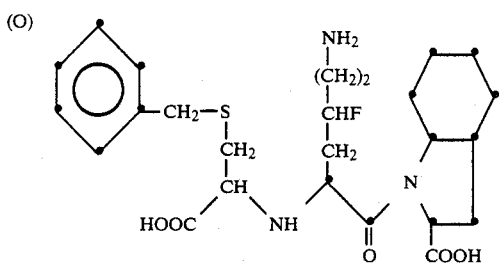

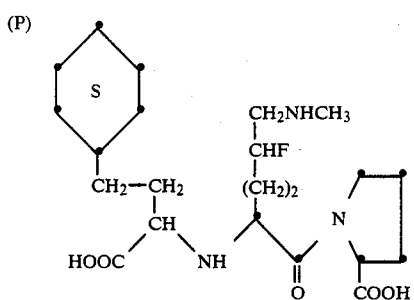

What is claimed is:

1. A compound which is a member of the group:

N²-[1(S)-carboxy-3-phenylpropyl]-(4-hydroxy-L-lysyl)-L-proline;

N²-[1(S)-ethoxycarbonyl-3-phenylpropyl]-[5-hydroxy-L-lysyl]-L-proline;

N-[1(S)-carboxy-3-phenylpropyl]-4-fluoro-L-lysyl)-L-proline; and,

N-[1(S)-carboxy-3-phenylpropyl]-(3-fluoro-L-ornithyl)-L-proline.

2. A pharmaceutical composition useful in treating hypertension comprising a pharmaceutically acceptable carrier and an antihypertensively effective amount of a compound of claim 1.

3. A composition of claim 2 wherein said compound is a member selected from the group consisting essentially of:

N²-[1(S)-carboxy-3-phenylpropyl]-(4-hydroxy-L-lysyl)-L-proline;

N²-[1(S)-ethoxycarbonyl-3-phenylpropyl]-[5-hydroxy-L-lysyl]-L-proline;

N-[1(S)-carboxy-3-phenylpropyl]-(4-fluoro-L-lysyl)-L-proline; and,

N-[1(S)-carboxy-3-phenylpropyl]-(3-fluoro-L-ornithyl)-L-proline.

4. A method of treating hypertension comprising administering to a patient in need of such treatment an antihypertensively effective amount of a compound of claim 1.

5. The method of claim 4 wherein said compound is a member selected from the group consisting essentially of:

N²-[1(S)-carboxy-3-phenylpropyl]-(4-hydroxy-L-lysyl)-L-proline;

N²-[1(S)-ethoxycarbonyl-3-phenylpropyl]-[5-hydroxy-L-lysyl]-L-proline;

N-[1(S)-carboxy-3-phenylpropyl]-4-fluoro-L-lysyl)-L-proline; and,

N-[1(S)-carboxy-3-phenylpropyl]-(3-fluoro-L-ornithyl)-L-proline.

* * * * *